(12) United States Patent
Bor et al.

(10) Patent No.: US 9,820,647 B2
(45) Date of Patent: Nov. 21, 2017

(54) SYSTEMS AND METHODS FOR MEASURING POSITION AND BOUNDARY OF LENS CAPSULE AND IMPLANTED INTRAOCULAR LENS IN EYE IMAGING

(71) Applicant: ABBOTT MEDICAL OPTICS INC., Santa Ana, CA (US)

(72) Inventors: Zsolt Bor, San Clemente, CA (US); Anthony W. Dennison, Irvine, CA (US); Michael Campos, Fremont, CA (US); Peter Patrick De Guzman, Aliso Viejo, CA (US)

(73) Assignee: ABBOTT MEDICAL OPTICS INC., Santa Ana, CA (US)

( * ) Notice: Subject to any disclaimer, the term of this patent is extended or adjusted under 35 U.S.C. 154(b) by 0 days.

(21) Appl. No.: 14/968,755

(22) Filed: Dec. 14, 2015

(65) Prior Publication Data

US 2016/0095515 A1  Apr. 7, 2016

Related U.S. Application Data

(63) Continuation of application No. 14/199,496, filed on Mar. 6, 2014, now Pat. No. 9,265,419.

(60) Provisional application No. 61/800,346, filed on Mar. 15, 2013.

(51) Int. Cl.
| | |
|---|---|
| *A61B 3/14* | (2006.01) |
| *A61B 3/00* | (2006.01) |
| *A61B 3/117* | (2006.01) |
| *A61B 3/10* | (2006.01) |
| *A61B 3/135* | (2006.01) |

(52) U.S. Cl.
CPC .......... *A61B 3/1173* (2013.01); *A61B 3/0025* (2013.01); *A61B 3/10* (2013.01); *A61B 3/135* (2013.01); *A61B 3/14* (2013.01)

(58) Field of Classification Search
USPC .................................................. 351/200–246
See application file for complete search history.

(56) References Cited

U.S. PATENT DOCUMENTS

| | | |
|---|---|---|
| 4,665,913 A | 5/1987 | L'Esperance, Jr. |
| 4,669,466 A | 6/1987 | L'Esperance |
| 4,732,148 A | 3/1988 | L'Esperance, Jr. |
| 4,770,172 A | 9/1988 | L'Esperance, Jr. |
| 4,773,414 A | 9/1988 | L'Esperance, Jr. |
| 5,108,388 A | 4/1992 | Trokel et al. |
| 5,163,934 A | 11/1992 | Munnerlyn |
| 5,207,668 A | 5/1993 | L'Esperance, Jr. |
| 5,219,343 A | 6/1993 | L'Esperance, Jr. |
| 5,646,791 A | 7/1997 | Glockler |

(Continued)

*Primary Examiner* — Mohammed Hasan
(74) *Attorney, Agent, or Firm* — Abbott Medical Optics Inc.

(57) ABSTRACT

Embodiments of this invention generally relate to systems and methods for eye imaging, and more particularly to measuring the size and position of the lens capsule and of the implanted intraocular lens. In one embodiment, a method for measuring the size and position of the lens capsule and of the implanted intraocular lens comprises generating and emitting one or more light beams at an angle adjacent to the eye, generating one or more eye images, and detecting the position and/or boundary of a lens capsule from its shadow casted by reflected light on the iris.

20 Claims, 8 Drawing Sheets

(56) References Cited

U.S. PATENT DOCUMENTS

| | | | |
|---|---|---|---|
| 7,261,415 B2* | 8/2007 | Chernyak | A61B 3/1015 351/209 |
| 7,338,169 B2 | 3/2008 | Somani | |
| 7,931,371 B2 | 4/2011 | Dai | |
| 8,394,084 B2* | 3/2013 | Palankar | A61F 9/00736 606/5 |
| 8,888,286 B2* | 11/2014 | Grenon | A61B 3/101 351/206 |
| 9,265,419 B2* | 2/2016 | Bor | A61B 3/14 |
| 2008/0123052 A1 | 5/2008 | Su et al. | |
| 2014/0176906 A1 | 6/2014 | Chen | |

* cited by examiner

SYSTEMS AND METHODS FOR MEASURING POSITION AND BOUNDARY OF LENS CAPSULE AND IMPLANTED INTRAOCULAR LENS IN EYE IMAGING

CROSS-REFERENCE TO RELATED APPLICATIONS

The present application claims priority to and is a continuation application of U.S. patent application Ser. No. 14/199,496, filed Mar. 6, 2014, now U.S. Pat. No. 9,265,419, which claims priority to U.S. Provisional Application No. 61/800,346 filed Mar. 15, 2013, which are hereby incorporated by reference in their entirety.

FIELD OF THE INVENTION

Embodiments of the present invention generally relate to eye imaging, and more particularly to measuring the size and position of the lens capsule and of the implanted intraocular lens based on eye imaging.

BACKGROUND OF THE INVENTION

Current ophthalmic diagnostic and measurement systems typically use wavefront acquisition and diagnostic capabilities to deliver measurement accuracy, enhancing the precision of laser vision correction surgery. An exemplary ophthalmic diagnostic and measurement product utilizing wavefronts is the Abbott Medical Optics (AMO) WaveScan WaveFront™ System, which, among having other capabilities and technologies, uses a Shack-Hartmann wavefront sensor that can quantify aberrations throughout the entire optical system of the patient's eye, including second-order aberrations related to spherical error and cylindrical errors, and higher-order aberrations related to coma, trefoil, and spherical aberrations. An exemplary wavefront diagnostic system was described in U.S. Pat. No. 7,931,371 to Dai, and is herein incorporated by reference in its entirety.

In addition to its use in ophthalmic diagnostic and measurement systems, laser technology has become the technique of choice for ophthalmic surgical applications, such as refractive surgery for correcting myopia, hyperopia, astigmatism, and so on, as well as surgery for treating and removing a cataractous lens. Known laser-assisted ophthalmic surgical systems typically use a variety of laser forms and/or laser energies to affect the correction, including infrared lasers, ultraviolet lasers, femtosecond lasers, wavelength multiplied solid-state lasers, and the like. The laser-assisted ophthalmic surgical systems often also utilize wavefront diagnostic systems to measure accurately the refractive characteristics of a particular patient's eye.

A wavefront diagnostic system generally captures eye images during wavefront measurement. A pupil camera in an aberrometer captures images of the eye, illuminated by infrared LEDs designed as a symmetric configuration. These eye images are used, for example, for iris registration for laser vision correction. The eye image is essential for wavefront-guided corneal refractive surgery since it identifies the treatment area and is used for eye tracking. While current method for capturing eye images using wavefront are generally adequate for patient examinations, further improvements would be desirable, particularly in measuring the size and position of the lens capsule and of the implanted intraocular lens (IOL).

In addition, ophthalmic slit lamps also capture an anterior segment of an eye with a beam of light. An exemplary ophthalmic slit lamp was described in U.S. Pat. No. 7,338,169 to Somani, and is herein incorporated by reference in its entirety. Further improvement to ophthalmic slit lamps in measuring the size and position of the lens capsule and of the implanted intraocular lens would also be desirable.

SUMMARY OF THE INVENTION

The field of the invention relates to systems and methods for eye imaging and, more particularly, for measuring the size and position of the lens capsule (or capsular bag) and of the implanted intraocular lens. A method for measuring the size and position of the lens capsule and of the implanted intraocular lens comprises generating and emitting one or more light beams at an angle adjacent to the eye, generating one or more eye images, and detecting the position and/or boundary of a lens capsule from its shadow casted by reflected light on the iris.

Other systems, methods, features, and advantages of the invention will be or will become apparent to one with skill in the art upon examination of the following drawings and detailed description. It is intended that all such additional systems, methods, features, and advantages be included within this description, be within the scope of the invention, and be protected by the accompanying claims.

BRIEF DESCRIPTION OF THE DRAWINGS

In order to better appreciate how the above-recited and other advantages and objects of the inventions are obtained, a more particular description of the embodiments briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than depicted literally or precisely.

DETAILED DESCRIPTION OF THE PREFERRED EMBODIMENTS

The present invention is generally directed to systems and methods for measuring the size and position of the lens capsule (or capsular bag) and of the implanted intraocular lens in eye imaging. An embodiment of the invention generally detects the position and/or boundary of a lens capsule from its shadow casted by reflected light on the iris by illuminating the eye with one or more light beams at an angle adjacent to the eye.

The measuring of the size and position of the lens capsule and of the implanted intraocular lens as described in the preferred embodiments of the invention may be used in stand-alone ophthalmic diagnostic and measurement systems, in a slit lamp, in a laser eye surgery system having an integrated ophthalmic diagnostic and measurement system, in an eye tracking system of an ophthalmic surgical system, and the like.

Figure 1:
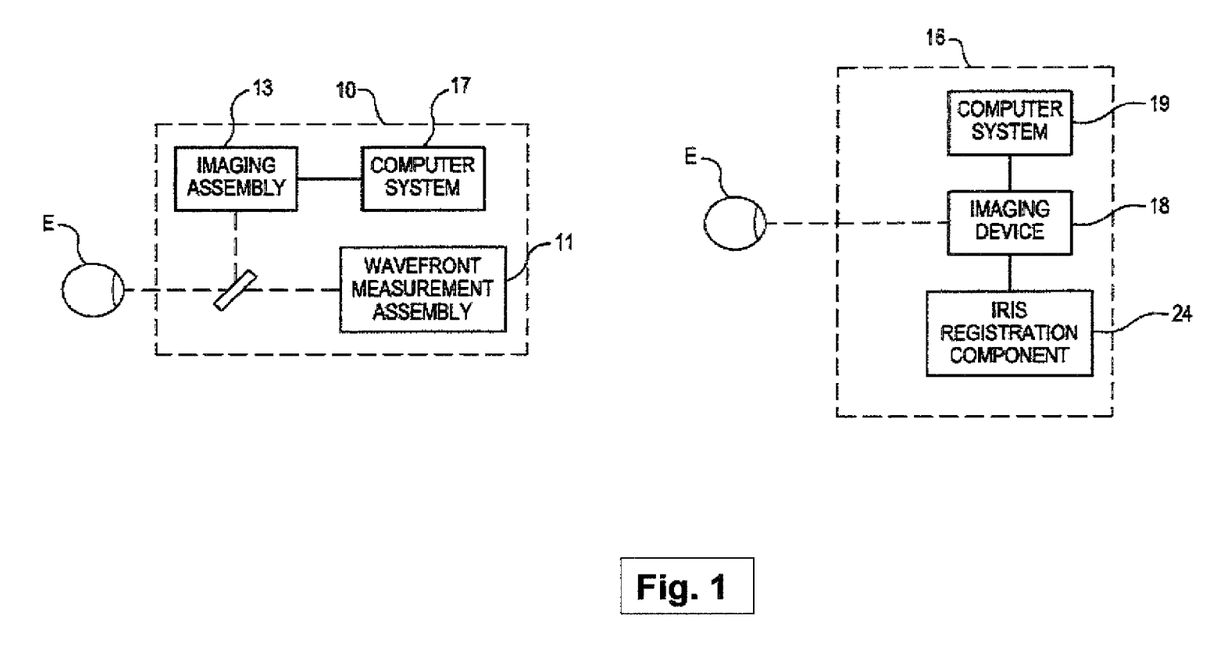
FIG. 1 schematically illustrates simplified measurement systems according to an embodiment of the present invention.

FIG. 1 illustrates a first measurement system 10 and a second measurement system 16. In an embodiment, the first measurement system 10 is a wavefront measurement device 10 that measures aberrations and other optical characteristics of an ocular or other optical tissue system. The data from such a wavefront measurement device may be analyzed by a computer system 17 and used to generate an optical surface from an array of optical gradients.

In another embodiment, the second measurement system 16 is a corneal topographer 16. Corneal topographer 16 may be used to diagnose and examine the corneal surface. Corneal topographer 16 typically includes an imaging device 18, such as a frame grabber that takes images of the cornea. The images obtained by the frame grabber are analyzed by a computer system 19, and the computer system 19 may generate one or more graphical and/or tabular outputs, including three dimensional topographical maps.

Figure 2:
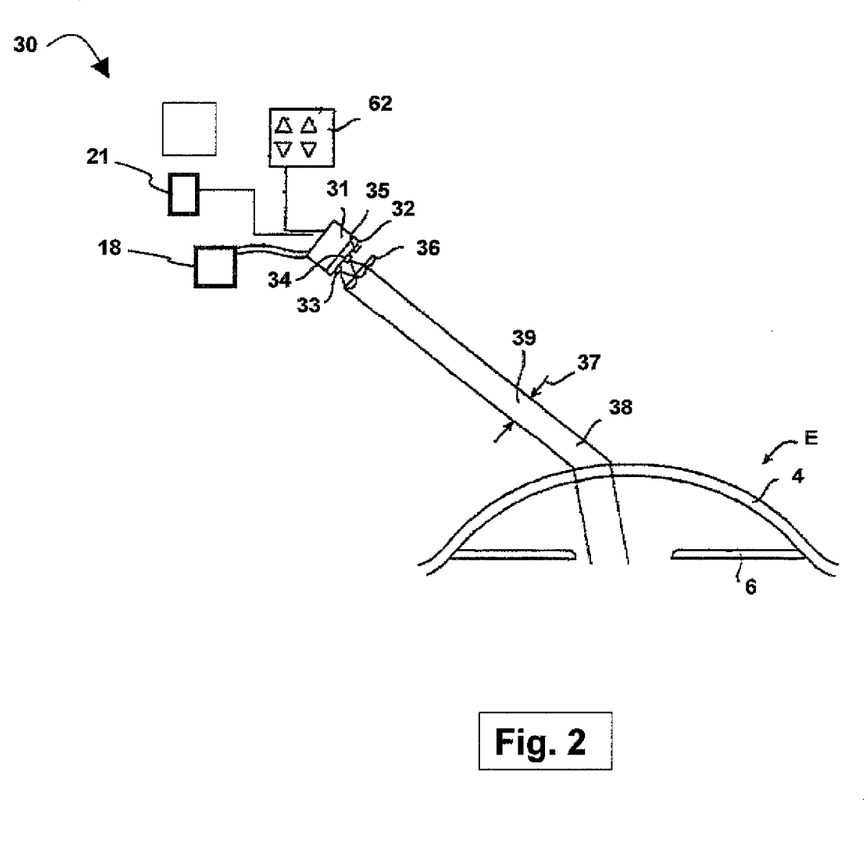
FIG. 2 is a perspective view of a slit lamp according to an embodiment of the present invention.

FIG. 2 illustrates, in an embodiment, an eye E having a cornea 4 and an iris 6 illuminated with a slit lamp 30 having a shaped beam of light 38 having a cross-section 39 with a size 37 across a cross-section 39. An LED array 32 is positioned near a micro-lens array 36. LED array 32 comprises a plurality of individual LEDs such as LEDs 33, 34 and 35. Micro-lens array 36 is positioned a focal length from the individual LEDs to collimate light emitted from the LEDs as the shaped light beam 38, which travels toward the eye E. In the example of FIG. 2, a portion of LED array 32 comprising LEDs 33 and 34 emits light. The size 37 across the cross-section 39 of the beam 38 is determined by a number of LEDs emitting light. An operator views the eye E through a microscope (not shown here, but for clarity, see incorporated U.S. Pat. No. 7,338,169 and other herein incorporated patents for further detail). An imaging device 18 may be mounted on the slit lamp 30 to image the eye E.

An LED driver (which may also be referred to herein as a computer system) 31 selectively drives any combination of LEDs 33, 34 and 35 of LED array 32. A user interface input device 62 is operationally coupled to the LED driver 31. The user interface input device 62 includes one more controls that adjust the size 37 across the cross-section 39 of the shaped light beam 38. The one or more controls of the user interface input device 62 also send one or more signals to the LED driver 31. The LED driver 31 selectively drives the LEDs of the LED array 32 in response to the one or more signals from the one or more controls. Another one or more controls of the user interface input 62 adjust an intensity of the light beam 38. An automated image analysis system 21 may be operatively coupled to the LED driver 31 to automatically adjust the light beam 38. For patient comfort, the visible part of the spectrum of the slit illumination can be filtered out using infrared (IR) glass filters, for example, filters RG715, RG830, RG850, or RG780 manufactured by SCHOTT North America, Inc, Elmsford, N.Y. One or more filters can be mounted in the filter turret (not shown) of the slit lamp illuminator.

Figure 3:
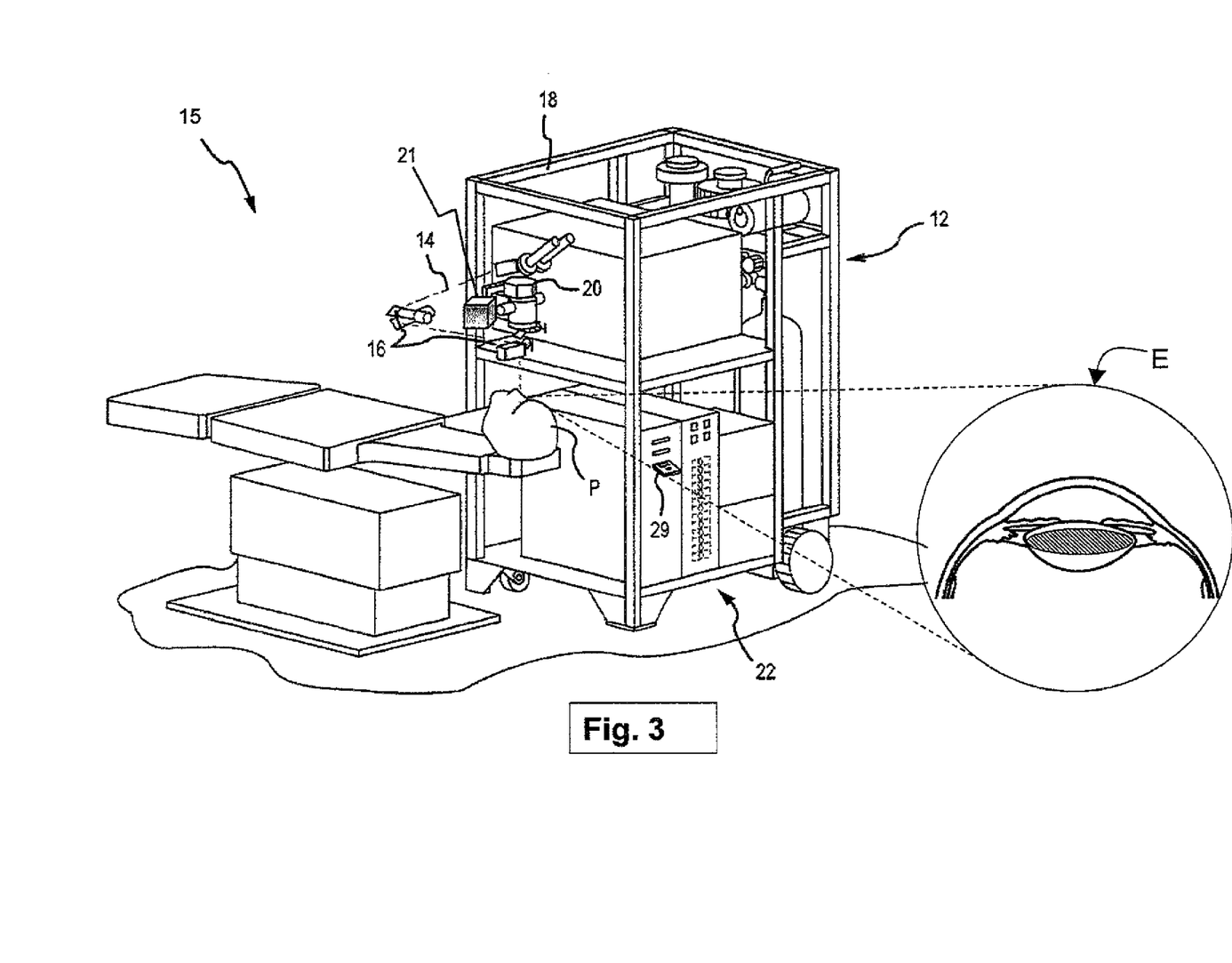
FIG. 3 is a perspective view of a laser eye surgery system according to an embodiment of the present invention.

FIG. 3 illustrates a laser surgery system 15. In an embodiment, the laser surgery system 15 includes a laser assembly 12 that produces a laser beam 14. Laser assembly 12 is optically coupled to laser delivery optics 16, which directs laser beam 14 to an eye E of a patient. An imaging assembly 20, including a microscope, is mounted on a delivery optics support structure (not shown here, but for clarity, see incorporated U.S. Pat. No. 7,931,371, and other herein incorporated patents for further detail) to image the cornea of eye E during the laser procedure. Laser assembly 12 generally comprises an excimer laser source, typically comprising an argon-fluorine laser producing pulses of laser light having a wavelength of approximately 193 nm. Laser assembly 12 may be designed to provide a feedback stabilized fluence at the patient's eye E, delivered via delivery optics 16. Although an excimer laser is the illustrative source of an ablating beam, other lasers may be used.

Laser assembly 12 and delivery optics 16 generally direct laser beam 14 to the eye E under the direction of a computer system 22. Computer system 22 may selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system will be under computer control of computer system 22 to affect the desired laser sculpting process so as to deliver a customized ablation profile, with the computer system 22 ideally altering the ablation procedure in response to inputs from an optical feedback system (not shown here, but for clarity, see incorporated U.S. Pat. No. 7,931,371 and other herein incorporated patents for further detail). The feedback may be input into computer system 22 from an automated image analysis system 21, or may be manually input into the processor by a system operator using a user input interface device 62 (FIG. 4) in response to a visual inspection of analysis images provided by the optical feedback system. Computer system 22 often continues and/or terminates a sculpting treatment in response to the feedback, and may optionally also modify the planned sculpting based at least in part on the feedback.

In an embodiment, surgery system 15 may use infrared LED as a light source.

Computer system 17, 19, 22, 31 may comprise (or interface with) a conventional or special computer, such as a personal computer (PC), laptop, and so on, including the standard user interface devices such as a keyboard, a mouse, a touch pad, foot pedals, a joystick, a touch screen, an audio input, a display monitor, and the like. Computer system 17, 19, 22, 31 typically includes an input device such as a magnetic or optical disk drive, or an input interface such as a USB connection, a wired and/or wireless network connection, or the like. Such input devices or interfaces are often used to download a computer executable code, to a storage media 29, embodying any of the methods of the present invention. Storage media 29 may take the form of an optical disk, a data tape, a volatile or non-volatile memory, RAM, or the like, and the computer system 17, 19, 22, 31 includes the memory and other standard components of modern computer systems for storing and executing this code. Storage media 29 may alternatively be remotely operatively coupled with computer system 17, 19, 22, 31 via network connections such as LAN, the Internet, or via wireless methods such as WLAN, Bluetooth, or the like.

Additional components and subsystems may be included with laser system 15, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference.

Figure 4:
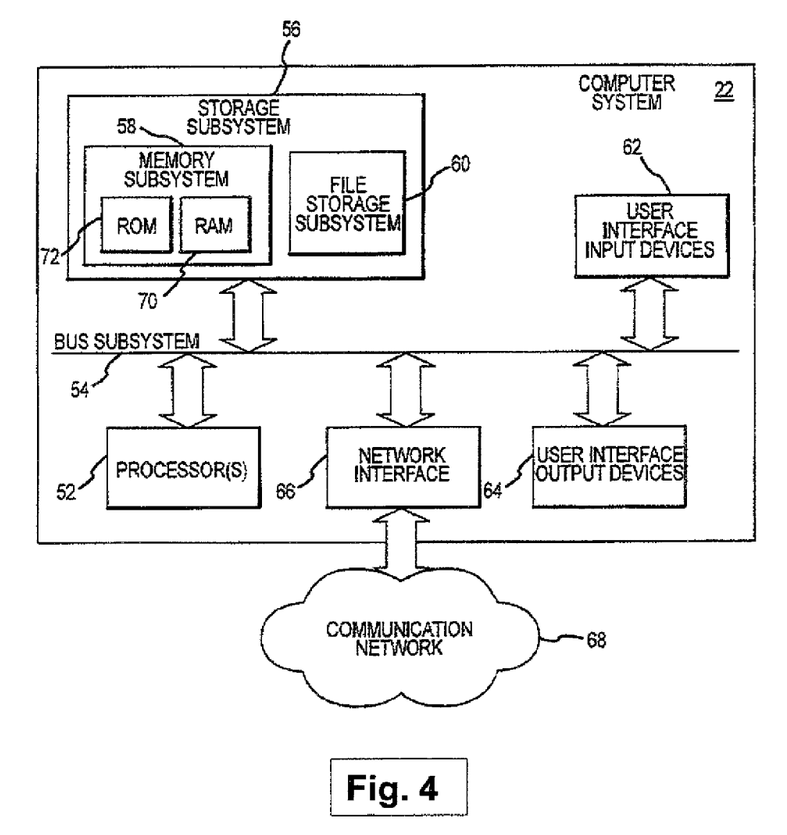
FIG. 4 is a simplified diagram of a computer system according to an embodiment of the present invention.

FIG. 4 is a simplified block diagram of an exemplary computer system 17, 19, 22, 31 that may be used in measurement instrument 10, measurement instrument 16, slit lamp 30, and laser surgical system 15. Computer system 17, 19, 22, 31 typically includes at least one processor 52 which may communicate with a number of peripheral devices via a bus subsystem 54. These peripheral devices may include a storage subsystem 56, comprising a memory subsystem 58 and a file storage subsystem 60 (which may include storage media 29), user interface input devices 62, user interface output devices 64, and a network interface subsystem 66. Network interface subsystem 66 provides an interface to outside networks 68 and/or other devices.

User interface input devices 62 may include a keyboard, pointing devices such as a mouse, trackball, touch pad, or graphics tablet, a scanner, foot pedals, a joystick, a touch screen incorporated into the display, audio input devices such as voice recognition systems, microphones, and other types of input devices. User interface input devices 62 are often used to download a computer executable code from a storage media 29 embodying any of the methods of the present invention. User interface input devices 62 are also used to control an eye fixation system. In general, use of the term "input device" is intended to include a variety of conventional and proprietary devices and ways to input information into computer system 17, 19, 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 17, 19, 22, 31 to a system operator.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include storage media 29 (FIG. 3). File storage subsystem 60 may include a hard disk drive along with associated removable media, a Compact Disk (CD) drive, an optical drive, DVD, solid-state removable memory, and/or other removable media cartridges or disks. One or more of the drives may be located at remote locations on other connected computers at other sites coupled to computer system 17, 19, 22, 31. The modules implementing the functionality of the present invention may be stored by file storage subsystem 60.

Bus subsystem 54 provides a mechanism for letting the various components and subsystems of computer system 17, 19, 22, 31 communicate with each other as intended. The various subsystems and components of computer system 17, 19, 22, 31 need not be at the same physical location but may be distributed at various locations within a distributed network. Although bus subsystem 54 is shown schematically as a single bus, alternate embodiments of the bus subsystem may utilize multiple busses.

Computer system 17, 19, 22, 31 itself can be of varying types including a personal computer, a portable computer, a workstation, a computer terminal, a network computer, a control system in a wavefront measurement system, a slit lamp, or laser surgical system, a mainframe, or any other data processing system. Due to the ever-changing nature of computers and networks, the description of computer system 17, 19, 22, 31 depicted in FIG. 4 is intended only as an example for purposes of illustrating one embodiment of the present invention. Many other configurations of computer system 17, 19, 22, 31 having more or fewer components than the computer system depicted in FIG. 4, are possible.

Figure 5:
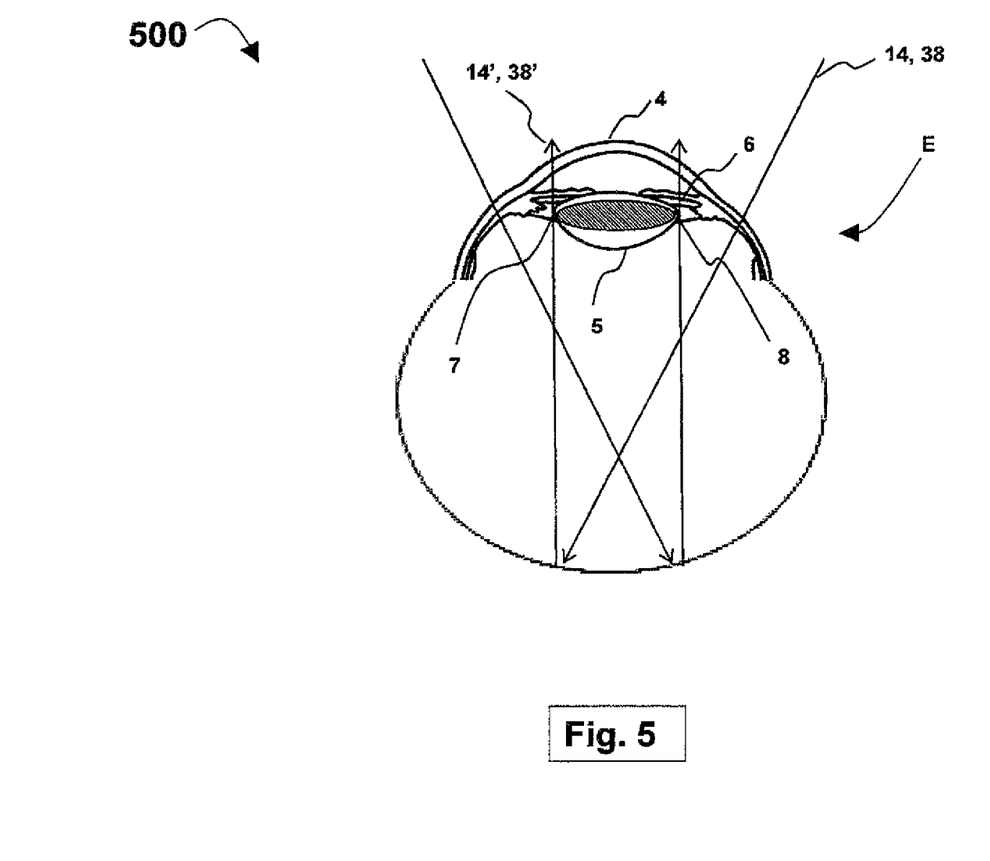
FIG. 5 shows an eye illumination according to an embodiment of the present invention.

FIG. 5 illustrates, in an embodiment, an exemplary technique 500 for measuring the size and position of the lens capsule and of the implanted intraocular lens. Measurement system 10, 16, or slit lamp 30, or laser surgery system 15 emits one or more laser beam 14 or light beam 38 into the eye E at an angle adjacent to the eye E. The one or more laser beam 14 or light beam 38 travels through the surface of the eye E and illuminates within the eye E. One or more laser beam 14' or light beam 38' reflects from inside the eye E and travels through iris 6 and cornea 4. An operator or software as described above carefully measures and/or adjusts the one or more laser beam 14 or light beam 38 such that one or more reflected laser beam 14' or light beam 38' travels through iris 6, including normal and healthy iris 6, and cornea 4, but travels less or does not travel through the lens capsule 5. The operator or software operatively controls the imaging device 18 to capture one or more images of the eye E digitally.

Figure 6:
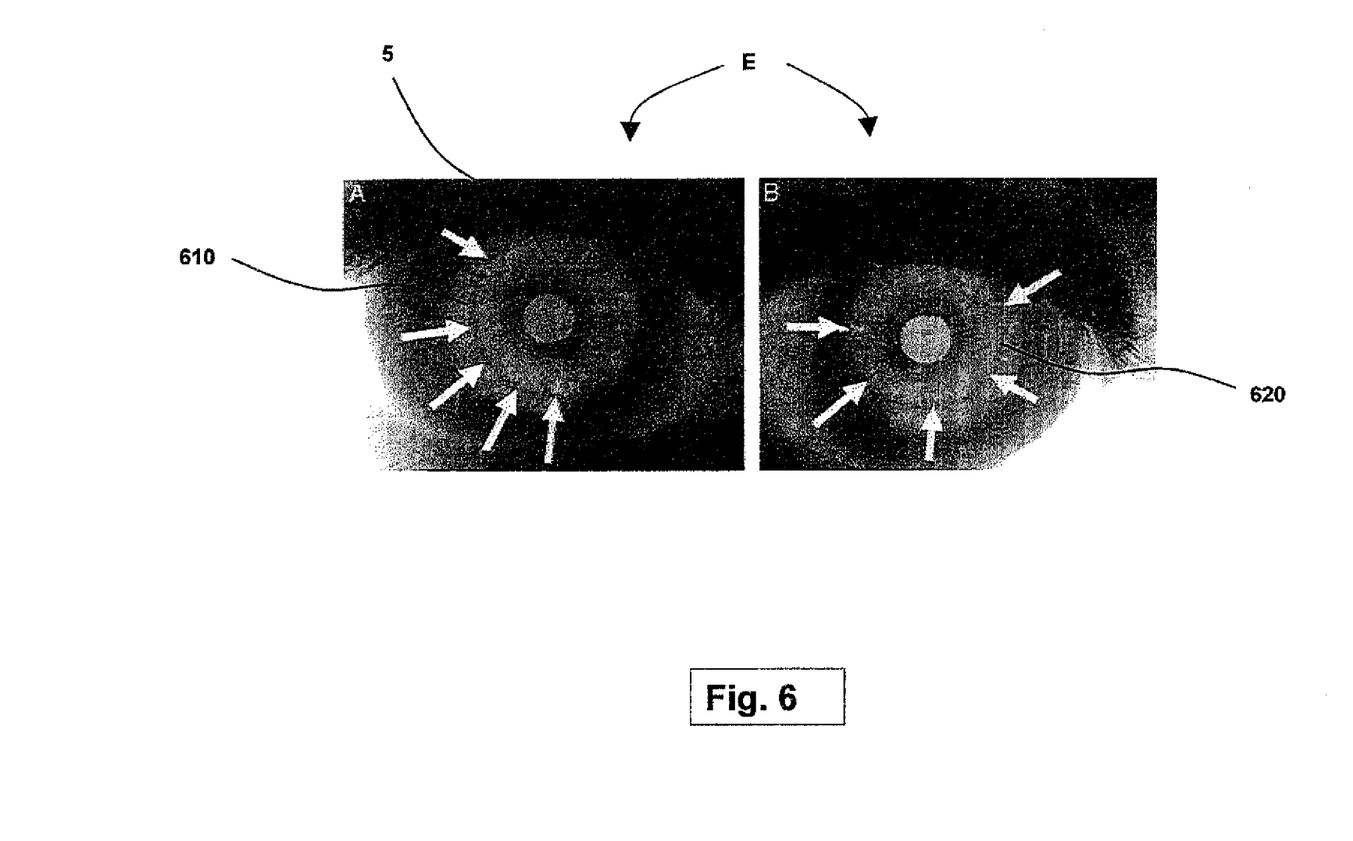
FIG. 6 shows exemplary eye images according to an embodiment of the present invention.

FIG. 6, in an embodiment, illustrates how the position and boundary 610, 620 of the lens capsule 5 can be detected and captured digitally as the laser beam 14' or light beam 38' reflects out of the eye E from within the eye E. The position and boundary 610, 620 of the lens capsule 5 are detected most clearly with light colored, such as blue, irises. The operator or software can measure the diameter and decentration x and y parameters of the lens capsule 5. The operator or software may use the detected measurements of the lens capsule 5 over multiple examinations to detect any change in the size of the lens capsule 5.

Figure 7:
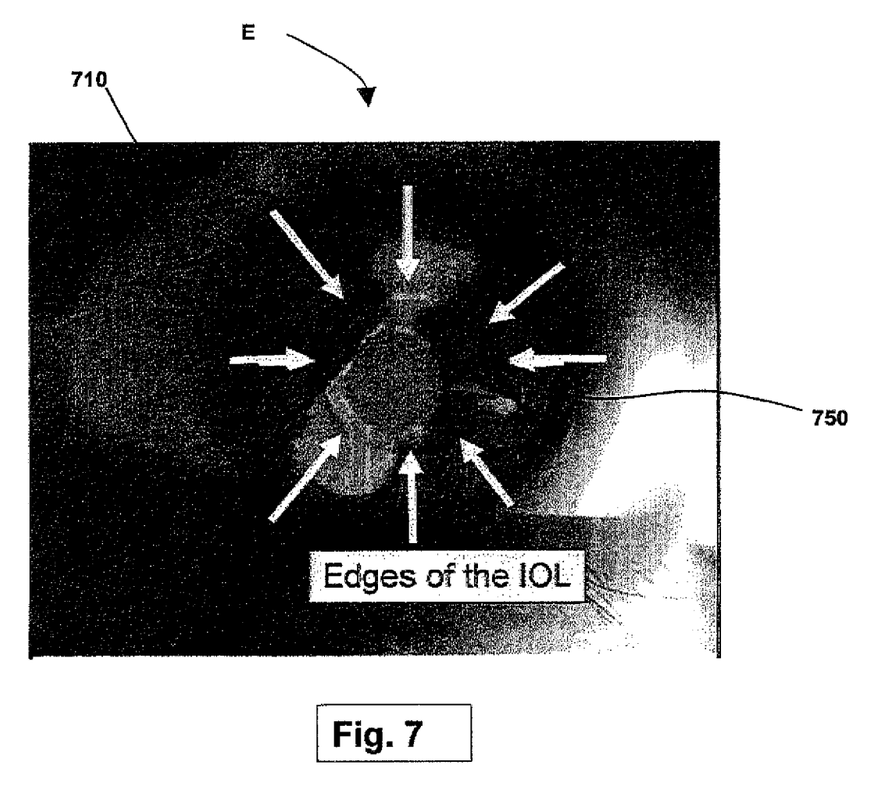
FIG. 7 shows another exemplary eye image according to an embodiment of the present invention.

FIG. 7, in an embodiment, illustrates how the position and boundary 710 of an implanted intraocular lens (IOL) 750 can be detected and digitally captured as the laser beam 14' or light beam 38' reflects out of the eye E from within the eye E. During an IOL implant operation, having the position of the lens capsule accurately detected, the operator can center the IOL properly. After the IOL implant operation, the operator can use the detected position of the IOL to measure any decentration. During subsequent examinations, the operator can also use the subsequently detected position of the IOL to treat any IOL decentration.

In cases where the patient is undergoing laser cataract surgery, and the capsular incision (capsulotomy) is being performed with a laser, the detected lens capsule position and centroid can be calculated from the acquired image. This information can then be input into the laser delivery system, which can then place the capsulotomy centrally with respect to the lens, rather than with respect to the iris or limbus. This may be especially important for accommodating IOLs, as their designs can differ greatly from traditional monofocal IOLs, and may have capsulotomy requirements particular to the brand of accommodating IOL.

Imaging the capsule bag and it decentration from the un-dilated iris pre-op to cataract surgery can also prove useful for customized IOL constructs. All IOLs have some form of a haptic structure, which are the non-optical struts that hold the IOL in the center of the capsule. However, if the center of the capsule is not centered with respect to the iris under un-dilated, non-surgical conditions, the IOL may not be positioned for optical vision quality. Having the decentration of the capsule quantified can allow for non-symmetric haptic design, where the IOL is non centered with respect to the capsule, but is centered with respect to the post-op iris.

Figure 8:
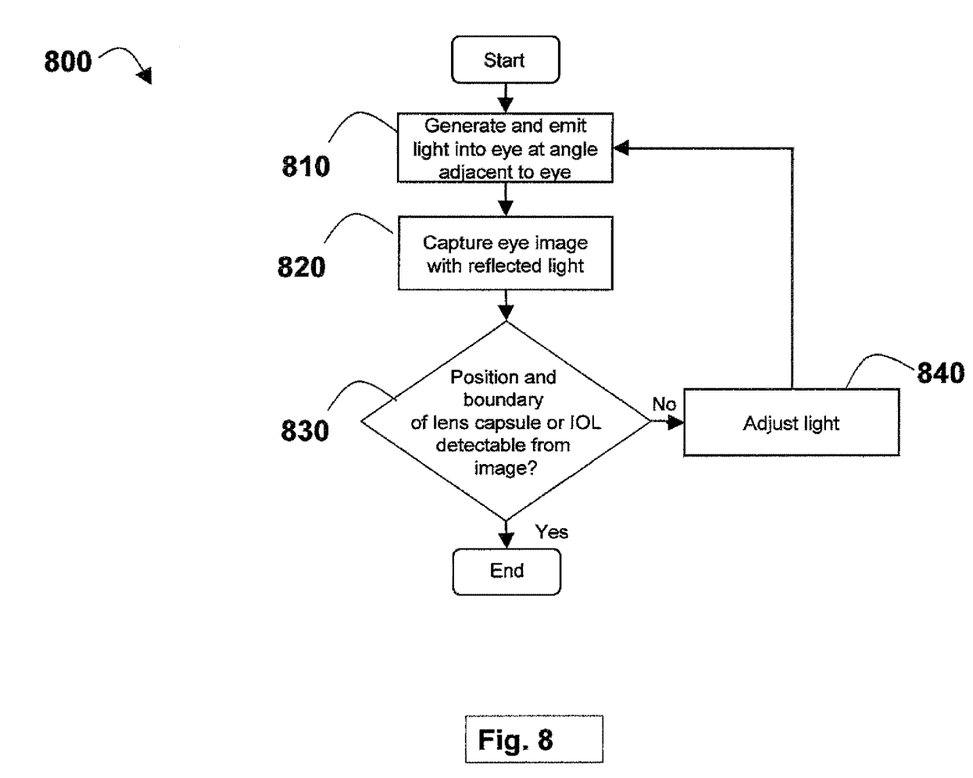
FIG. 8 is a flowchart illustrating a process according to an embodiment of the present invention.

FIG. 8 shows a process 800 for measuring the size and position of the lens capsule and of the implanted intraocular lens. The process starts with the measurement system, slit lamp, or laser surgery system generates and emits light at an angle adjacent to and into a patient eye (Action Block 810). With the light reflected from within the eye, the measurement system, slit lamp, or laser surgery system then captures an image of the eye (Action Block 820). The measurement system, slit lamp, or laser surgery system determines whether the position and boundary of the lens capsule or of the implanted intraocular lens (IOL) can be detected from the image (Decision Block 830). If the position and boundary of the lens capsule or of the implanted IOL cannot be detected from the image, the measurement system, slit lamp, or laser surgery system adjusts the light (Action Block 840) and repeats the step of generating and emitting light into the patient's eye (Action Block 810) until the position and boundary of the lens capsule or of the implanted IOL can be detected.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein are merely illustrative, and that the invention may appropriately be performed using different or additional process actions, or a different combination or ordering of process actions. For example, while this invention is particularly suited for measuring the size and position of the lens capsule and of the implanted intraocular lens, it can be used for any other ophthalmic application and surgical system.

Although embodiments of this invention are described and pictured in an exemplary form with a certain degree of particularity, describing the best mode contemplated of carrying out the invention, and of the manner and process of making and using it, those skilled in the art will understand that various modifications, alternative constructions, changes, and variations can be made in the ophthalmic interface and method without departing from the spirit or scope of the invention. Thus, it is intended that this invention cover all modifications, alternative constructions, changes, variations, as well as the combinations and arrangements of parts, structures, and steps that come within the spirit and scope of the invention as generally expressed by the following claims and their equivalents.

What is claimed is:

1. An eye imaging method comprising:
   (a) using an illumination device, generating one or more light beams and directing them into a patient's eye;
   (b) using an imaging device, capturing one or more images of the patient's eye; and
   (c) detecting a position or boundary of a lens capsule of the patient's eye within the one or more captured images of the patient's eye.

2. The eye imaging method of claim 1, further comprising:
   adjusting the one or more light beams until the position or boundary of the lens capsule is detected in the one or more captured images.

3. The eye imaging method of claim 1, wherein in step (a), the one or more light beams are infrared (IR) light beams.

4. The eye imaging method of claim 1, wherein in step (a), the one or more light beams are shaped beams of light generated by using a slit lamp.

5. The eye imaging method of claim 4, wherein step (a) includes using at least one infrared (IR) glass filter to filter part of the spectrum of the beams generated by the slit lamp.

6. The eye imaging method of claim 5, wherein step (a) further includes mounting the at least one infrared (IR) glass filter in a filter turret of the slit lamp.

7. The eye imaging method of claim 1, wherein step (c) includes detecting the position or boundary of the lens capsule from its shadow casted by reflected light on an iris of the eye.

8. An eye imaging method comprising:
   (a) using an illumination device, generating one or more light beams and directing them into a patient's eye;
   (b) using an imaging device, capturing one or more images of the patient's eye; and
   (c) detecting a position or boundary of an intraocular lens in the patient's eye within the one or more captured images of the patient's eye.

9. The eye imaging method of claim 8, further comprising:
   adjusting the one or more light beams until the position or boundary of the intraocular lens is detected in the one or more captured images.

10. The eye imaging method of claim 8, wherein in step (a), the one or more light beams are infrared (IR) light beams.

11. The eye imaging method of claim 8, wherein in step (a), the one or more light beams are shaped beams of light generated by using a slit lamp.

12. The eye imaging method of claim 11, wherein step (a) includes using at least one infrared (IR) glass filter to filter part of the spectrum of the beams generated by the slit lamp.

13. The eye imaging method of claim 12, wherein step (a) further includes mounting the at least one infrared (IR) glass filter in a filter turret of the slit lamp.

14. The eye imaging method of claim 8, wherein step (c) includes detecting the position or boundary of the intraocular lens from its shadow casted by reflected light on an iris of the eye.

15. An eye imaging method for detecting a position or boundary of a lens capsule or an intraocular lens in a patient's eye, comprising:
- (a) using an illumination device, generating one or more light beams and directing them into the patient's eye;
- (b) using an imaging device, capturing one or more images of the patient's eye;
- (c) operatively coupling a control system including a processor and a user interface input device to the illumination device and the imaging device;
- (d) detecting a position or boundary of the lens capsule or the intraocular lens in the patient's eye within the one or more captured images of the patient's eye; and
- (e) using the user interface input device, adjusting the one or more light beams until the position or boundary of the lens capsule or the intraocular lens is detected.

16. The eye imaging method of claim 15, further comprising:
measuring the one or more light beams using the processor.

17. The eye imaging method of claim 15, wherein in step (a), the illumination device generates the one or more light beams using a laser.

18. The eye imaging method of claim 15, wherein in step (a), the illumination device generates the one or more light beams using an infrared laser.

19. The eye imaging method of claim 15, wherein in step (a), the illumination device generates a shaped beam of light using a slit lamp.

20. The eye imaging method of claim 19, wherein step (a) includes using at least one infrared (IR) glass filter to filter part of the spectrum of the beam generated by the slit lamp.

* * * * *